United States Patent
Saito

(10) Patent No.: US 9,162,224 B2
(45) Date of Patent: Oct. 20, 2015

(54) DEVICE AND METHOD FOR MANUFACTURING THE SAME

(71) Applicant: CANON KABUSHIKI KAISHA, Tokyo (JP)

(72) Inventor: Tomohiro Saito, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 217 days.

(21) Appl. No.: 13/693,349

(22) Filed: Dec. 4, 2012

(65) Prior Publication Data
US 2013/0156657 A1    Jun. 20, 2013

(30) Foreign Application Priority Data
Dec. 20, 2011 (JP) ................ 2011-277996

(51) Int. Cl.
| | |
|---|---|
| B23P 15/00 | (2006.01) |
| B01L 3/00 | (2006.01) |
| H01L 21/28 | (2006.01) |
| G01N 27/447 | (2006.01) |
| B81C 1/00 | (2006.01) |
| H01L 41/00 | (2013.01) |
| H01L 21/00 | (2006.01) |
| H01L 41/313 | (2013.01) |
| B01L 7/00 | (2006.01) |

(52) U.S. Cl.
CPC .......... *B01L 3/502707* (2013.01); *B23P 15/00* (2013.01); *B81C 1/00817* (2013.01); *G01N 27/44791* (2013.01); *B01L 3/502715* (2013.01); *B01L 7/52* (2013.01); *B01L 2300/0645* (2013.01); *B01L 2300/0887* (2013.01); *B01L 2300/12* (2013.01); *B01L 2300/1805* (2013.01); *B01L 2300/1827* (2013.01); *B81B 2201/051* (2013.01); *H01L 21/28* (2013.01); *H01L 41/313* (2013.01); *Y10T 29/494* (2015.01)

(58) Field of Classification Search
None
See application file for complete search history.

(56) References Cited

U.S. PATENT DOCUMENTS

| | | | | |
|---|---|---|---|---|
| 2005/0104479 | A1* | 5/2005 | Xu et al. | 310/334 |
| 2007/0190685 | A1* | 8/2007 | Ebbutt | 438/106 |
| 2012/0266974 | A1* | 10/2012 | Kitamoto | 137/341 |

FOREIGN PATENT DOCUMENTS

| | | |
|---|---|---|
| JP | 9-162513 A | 6/1997 |
| JP | 11-186263 A | 7/1999 |
| JP | 2003-202678 A | 7/2003 |

* cited by examiner

*Primary Examiner* — Lyle Alexander
*Assistant Examiner* — Jennifer Wecker
(74) *Attorney, Agent, or Firm* — Fitzpatrick, Cella, Harper & Scinto

(57) ABSTRACT

It is an object of this invention to prevent a resistor material and an electrode material from diffusing and suppress variation in electric resistance. In a device including a plurality of metal layers of different compositions on a substrate and a second structure made of a material, such as glass paste, requiring a firing process at the time of formation, an intermediate layer is formed between a first metal layer and a second metal layer forming the first structure. The intermediate layer is of an intermetallic compound including one or more metallic elements in the first metal layer and one or more metallic elements in the second metal layer. The melting point of the intermetallic compound is higher than a firing temperature when the second structure is formed, and the intermetallic compound is produced at a temperature higher than the firing temperature for forming the second structure.

25 Claims, 2 Drawing Sheets

DEVICE AND METHOD FOR MANUFACTURING THE SAME

BACKGROUND OF THE INVENTION

1. Field of the Invention

The present invention relates to a device including a structure which is made of a material requiring a firing process at the time of manufacture and a method for manufacturing the device.

2. Description of the Related Art

Various apparatuses and sensors have been developed to observe the course of a biochemical reaction or to obtain a result of a chemical analysis. As one of the apparatuses and sensors, there is proposed a microdevice which has a fine structure of predetermined fluid channel shape, such as a microchannel, in a substrate. Microdevices of this type have been miniaturized using, e.g., a semiconductor manufacturing method, and the whole analysis process leading to obtainment of desired information can be performed on the microdevices.

Such devices are called micro-total analysis systems (μ-TAS) or labs-on-a-chip. Structures including a fine structure, such as a microchannel, in a substrate are called microfluidic devices.

The microdevices are expected, due to minuteness of the amount of an analyte, to decrease in the amount required of a reagent due to a reduction in the amount of fluid contained in the devices and decrease in reaction time, compared with conventional desktop-size analytical instruments.

In a microdevice in which a heater (resistor) is arranged in a microfluid channel to heat fluid passing through the microfluid channel, since the volume of fluid is small, the temperature of fluid quickly tracks the operation of the heater, and the the temperature of fluid can quickly be raised and lowered. Use of such a microdevice allows a more rapid PCR reaction of DNA.

Since many of microdevices as described above including a microfluid channel are based on a glass substrate, machining of a fine fluid channel can be laborious or difficult. For example, the machining requires micromachining technology, such as machining a glass substrate by etching. For this reason, microdevices are costly to manufacture, which leads to the need for an inexpensive machining method. Under the circumstances, there is devised formation of microdevices without micromachining technology, by employing printing using, e.g., glass paste, or lithography technology (see Japanese Patent Application Laid-Open No. 2003-202678).

If a device, including a structure (first structure) which includes metal layers and a structure (second structure) made of a material (e.g., glass frit or glass paste) requiring a firing process at the time of formation, such as a microfluidic device, is fabricated by glass paste printing, lithography technology, or the like, the entire device is subjected to a high temperature at the time of firing of the second structure. At this time, according to the findings of the present inventors, since the first structure is also brought to a temperature close to the high temperature, materials for the metal layers of the first structure interdiffuse due to heat of the firing, and the electric resistance value of a part of the device may unintentionally vary.

For example, in the case of a microfluid channel, the electric resistance value between a heater (made of, e.g., Pt) constituting a first structure and an extraction electrode (made of, e.g., Au) may vary, and the amount of the variation depends on the connection status (e.g., area and thickness) between the components. Consequently, if the interdiffusion occurs, the variability of the electric resistance value increases. If a heat treatment process is repeated a plurality of times, the status of interdiffusion changes with each iteration, and the variability increases further. It is difficult to control the amount of variation in electric resistance value by a process, which therefore creates a need to correct a driving condition for each of heaters on a device. In order to obtain correction values, the electric resistance values of the heaters need to be individually measured. This is so laborious and it reduces operating efficiency.

There is also available a process of inserting an intermediate layer which inhibits diffusion between two components, as disclosed in Japanese Patent Application Laid-Open No. H09-162513. However, if high-temperature heat treatment, such as firing of glass frit or glass paste, is performed, a material for the intermediate layer may diffuse.

There is further available a process of inserting a layer of an intermetallic compound having a high melting point as an intermediate layer, like the method disclosed in Japanese Patent Application Laid-Open No. H11-186263. The intermetallic compound itself, however, also diffuses at a heat-treatment temperature at which glass frit or glass paste is fired.

SUMMARY OF THE INVENTION

The present invention has as an object to provide a method for forming an intermediate layer capable of suppressing variation in electric resistance between metals, of which a first structure including metal layers is made, even when high-temperature heat treatment, such as firing glass frit or glass paste, is performed.

According to the present invention, in a device including a first structure which includes a plurality of metal layers of different compositions on a substrate and a second structure made of a material, such as glass frit or glass paste, requiring a firing process at the time of formation, an intermediate layer is formed between a first metal layer and a second metal layer forming the first structure. The intermediate layer is of an intermetallic compound including one or more metallic elements in the first metal layer and one or more metallic elements in the second metal layer. A melting point of the intermetallic compound is higher than a firing temperature when the second structure is formed, and the intermetallic compound is produced at a temperature higher than the firing temperature for forming the second structure.

After the intermediate layer of the intermetallic compound according to the present invention is formed, variation in electric resistance is reduced to ¹⁄₁₀₀ or less of variation in electric resistance of a case without an intermetallic compound layer, which is a great improvement.

Once an intermetallic compound is produced, variation in resistance is continuously suppressed unless heat treatment above a temperature at which the intermetallic compound is produced is performed.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

A manufacturing method using an intermediate layer made of an intermetallic compound which suppresses variation in electric resistance, according to the present invention, will be exemplary described below in the context of manufacture of a microfluidic device. Note that the present invention is not limited to manufacture of a microfluidic device to be described below and can be widely applied to manufacture of a device which has a bonded interface made of different materials and which is manufactured by high-temperature heat treatment of, e.g., glass frit or glass paste.

Note that although the example below will be described in the context of a structure in which a plurality of metal layers of different compositions is stacked as a first structure, a device subject to the present invention is not limited to such a structure. The present invention can be applied to any other device as long as the device includes a first structure including a plurality of metal layers of different compositions and a second structure made of a material requiring a firing process at the time of formation, and the first structure includes an intermediate layer according to the present invention among the plurality of metal layers. For example, metal layers constituting a first structure need not be stacked in a direction perpendicular to a substrate, and a plurality of metal layers of different compositions may be arranged in a lateral direction on a substrate, and an intermediate layer according to the present invention may be present among the metal layers. If a diffusion-preventing layer which is an intermediate layer according to the present invention and which can be used in context of thermal diffusion among the plurality of metal layers is formed among a plurality of metal layers constituting a first structure, the metal layers constituting the first structure and the intermediate layer need not be in contact with each other.

Figure 1A:
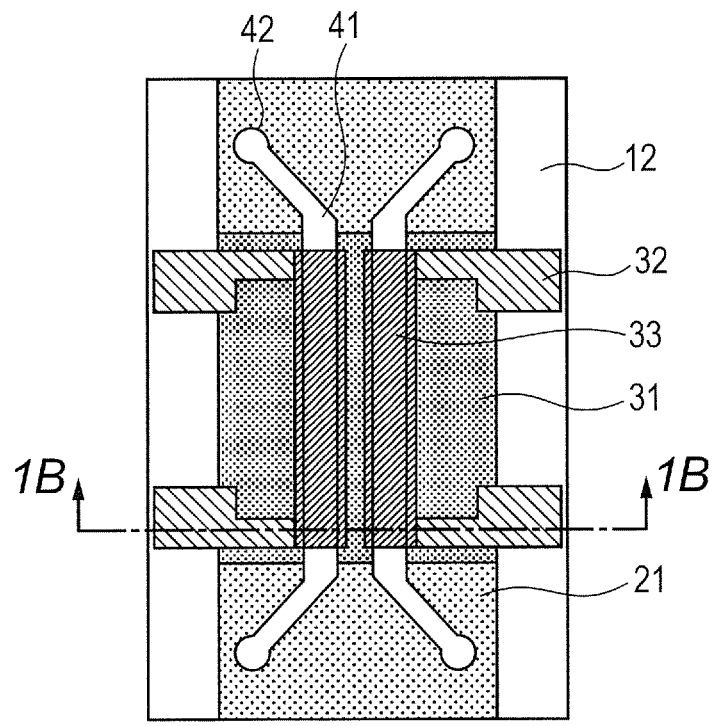
FIG. 1A is a plan view of a microfluid channel which is manufactured according to the present invention, as seen from above.
Figure 1B:
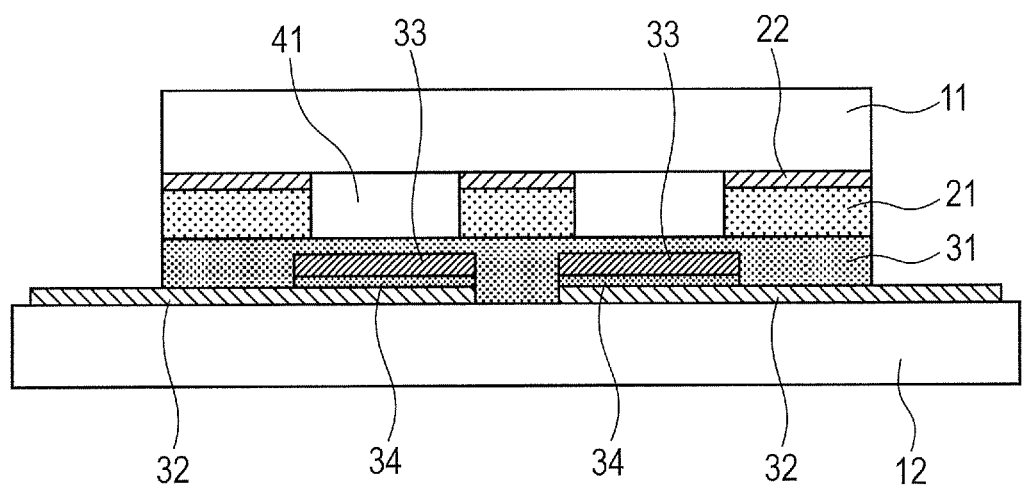
FIG. 1B is a cross-sectional view of FIG. 1A taken along line 1B-1B.

FIG. 1A is a plan view of an example of a microfluidic device which is a subject-matter of the present invention, and FIG. 1B is a cross-sectional view of FIG. 1A taken along lines 1B-1B. As illustrated in FIG. 1B, the microfluidic device includes, between a first substrate 11 and a second substrate 12, a resistor 33 (a first metal layer) having a heater function, an extraction electrode 32 (a second metal layer) which is electrically connected to the resistor 33, and an intermediate material 34 between the resistor 33 and the extraction electrode 32, which layers constituting a first structure, a resistor protective coat 31 on the resistor, a microfluid channel 41, a partition 21 (a second structure) for the microfluid channel, and a bonding material 22.

Note that a microfluidic device refers to a device including a microfluid channel in which a fluid flows as a laminar flow. A microfluid channel is a fluid channel having a Reynolds number (Re) of about 2000 or less in which the laminar flow occurs. A Reynolds number can be calculated by the following expression:

$$Re = \rho V d / \mu = V d / \nu$$

where $\rho$ is the density of a fluid, $\mu$ is the viscosity of the fluid, V is the flow velocity of the fluid in a tube, d is the diameter of the tube, and $\nu$ is the dynamic viscosity of the fluid.

The microfluid channel 41 is connected to the outside via holes 42 formed in the first substrate 11. The microfluid channel 41 is surrounded by the partition 21 and bonding material 22 and it is sealed such that a fluid passing through the microfluid channel 41 does not leak.

The resistor 33 is electrically connected to the extraction electrode 32. The resistor 33 can be heated by energizing the extraction electrode 32 from an external power source. The temperature can be measured by measuring the electric resistance of the resistor during heating.

Components of the microfluidic device will be described.

The first substrate 11 only needs to be transparent and translucent. For example, non-alkali glass, soda lime glass, high-strain point glass, quartz, or the like can be used as the material. The second substrate 12 only needs to have thermal resistance. Although the second substrate 12 need not necessarily be a transparent substrate, since the second substrate 12 is to be bonded to the first substrate, the coefficient of thermal expansion of the second substrate 12 is desirably close to the coefficient of thermal expansion of the first substrate. For example, non-alkali glass, soda lime glass, high-strain point glass, quartz, alumina, silicon nitride (SiN), or sapphire can be used as the material.

The material for the resistor 33 is desirably a material which is a metallic element or a compound containing a metallic element which can be heated by Joule heat resulting from electric resistance, and it is desirably linear in a temperature coefficient of electric resistance. Examples of the material include Pt, AuPt, AgPd, and AgRuO. The material for the extraction electrode 32 is desirably a metallic element which is low in electric resistance and insusceptible to surface oxidation. Examples of the material include Au, Ni, and Pt.

The material for the intermediate material 34 that is to be arranged between a resistor and an electrode is a metallic element or a compound containing a metallic element, between which and both the material for the resistor 33 and the material for the extraction electrode an intermetallic compound is produced by firing. Examples of the material for such an intermediate material include Ti, Zr, V, and Nb. The material for the intermediate material 34 is not limited to pure metals, and an intermetallic compound, between which and both the material for the resistor 33 and the material for the extraction electrode 32 an intermetallic compound is produced, may be used as the material for the intermediate material 34. In this case, a new intermetallic compound different from the intermetallic compound which is the material for the intermediate material 34 may be produced by diffusion. Examples of such an intermetallic compound that can be used as the material for the intermediate material include intermetallic compounds such as, $Ti_3Au$, $AuZr_3$, $V_3Au$, and $AuNb_3$.

An intermediate layer according to the present invention is of an intermetallic compound which is produced by thermal diffusion between the materials for the resistor and extraction electrode 32 and the material for the intermediate material 34. The material for the intermediate layer need not contain an element which is a material for the resistor or the electrode as long as such an intermetallic compound can be produced.

When the device according to the present invention is to be manufactured, alternatively, the material for the intermediate material 34 need not be prepared, and the intermetallic compound layer serving as the intermediate layer may also be formed between the first metal layer and the second metal layer by firing the material for the resistor 33 and the material for the extraction electrode 32.

In order to prevent interdiffusion from occurring again after formation of the intermediate layer in a manufacturing process (to be described later), an intermetallic compound whose melting point is higher than a firing temperature required in a subsequent device manufacturing process is selected as one serving as the intermediate layer according to the present invention.

The protective coat 31 provided aimed at insulating and protecting the resistor 33 is an insulator, and a material which is poorly reactive with a reagent to be run through a microfluid channel is desirable. Examples of the material include $SiO_2$ and SiN.

The material for the partition 21 is desirably a material which does not let a fluid passing through the microfluid channel 41 leak out and which is poorly reactive with a reagent to be run through the microfluid channel is desirable. Examples of the material include $Bi_2O_3$—$B_2O$ glass.

The material for the bonding material 22 that bonds together the first substrate and second substrate is not particularly limited and it only needs to be a commonly used material which has a negative temperature coefficient of viscosity and which is softened at high temperatures.

Since the microfluidic device according to the present invention includes a fluid channel above the first metal layer having a heater function through the protective coat 31, it can directly transfer heat to a fluid passing through the fluid channel.

Additionally, since a wall surface of each fluid channel facing the first metal layer are made of a material with optical transparency, emitted light in the fluid channel can be transmitted through the material and be detected.

Moreover, since side wall surfaces of each fluid channel are formed by firing glass frit or glass paste, the microfluidic device can be fabricated by a simple manufacturing process.

Another aspect of the fluidic device according to the present invention includes a substrate, a first metal layer formed on the substrate and having a heater function, a second metal layer which is an electrode electrically connected to the first metal layer, a material with optical transparency which serves as a wall surface of a fluid channel facing the first metal layer such that the fluid channel is formed above the first metal layer, and a third material which serves as side wall surfaces of the fluid channel and which is obtained by firing glass frit or glass paste, in which an intermediate layer is formed between the first metal layer and the second metal layer, and the intermediate layer is of an intermetallic compound containing one or more metallic elements, of which the first metal layer is made, and one or more metallic elements, of which the second metal layer is made.

The above-described configuration allows efficient and precise control of transfer of heat to a fluid in a fluid channel. A suitable fluidic device can thus be provided.

An example of a method for manufacturing the microfluidic device including an intermetallic compound layer according to the present invention will be described.

Step 1

Figure 2A:
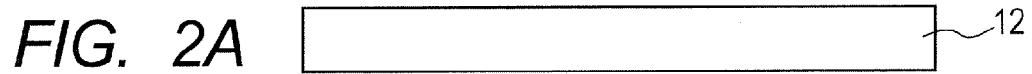
FIGS. 2A, 2B, 2C, 2D, 2E, 2F, 2G, and 2H are cross-sectional views illustrating an example of a specific process flow of a manufacturing method according to the present invention.
Figure 2B:
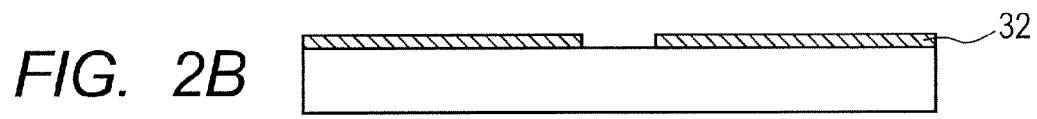
Figure 2C:
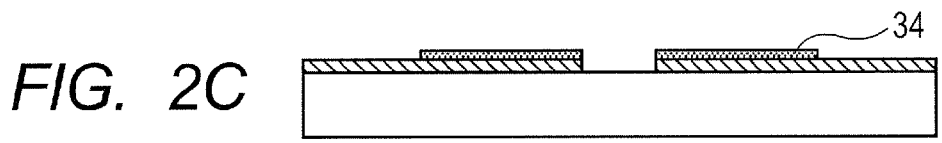
Figure 2D:
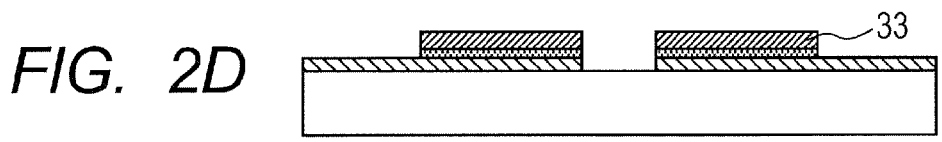

First, the second substrate 12 is prepared (FIG. 2A), and the extraction electrodes 32 are formed on the second substrate 12 (FIG. 2B). The intermediate material is formed on a part of each extraction electrode 32 where the resistor 33 is to contact (FIG. 2C). The resistor 33 is formed on each intermediate material 34 (FIG. 2D). The protective coat 31 is formed to cover the resistors 33 (FIG. 2E).

Known methods can be used for forming the extraction electrodes, intermediate materials, resistors, and protective coat.

Step 2

Figure 2E:
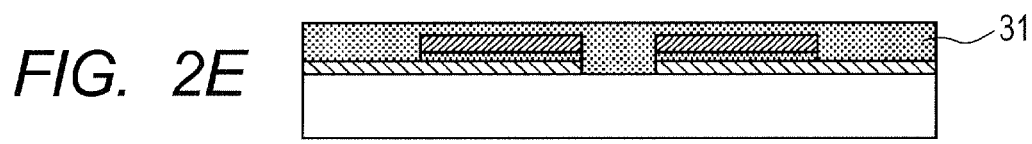

After formation of the resistors 33, intermediate materials 34, extraction electrodes 32, and protective coat 31 on the second substrate 12 is completed, heat treatment is performed to grow an intermetallic compound between the intermediate material 34 and the resistor 33 and extraction electrode 32 (FIG. 2E). The heat treatment needs to be performed at a temperature higher than the temperature for heat treatment in a subsequent process. A heating method and a heating atmosphere for the heat treatment are not particularly limited. The extraction electrodes may be heated in inert gas or under vacuum so as to prevent the extraction electrodes from being excessively oxidized. Electric resistance tends to become higher after an intermetallic compound is produced by the heat treatment than before the production. Hence, an amount by which resistance is increased by heat treatment is checked in advance, and the shape of each resistor is designed so as to achieve a desired resistance value.

Step 3

Figure 2F:
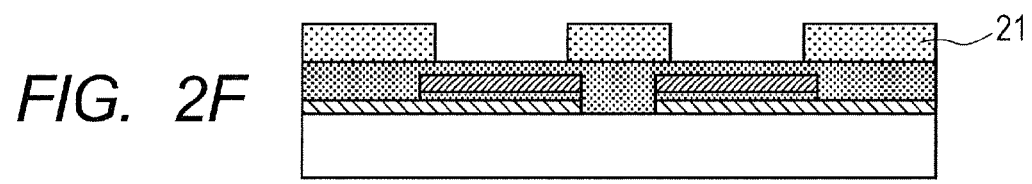

The partition 21 is formed on the protective coat (FIG. 2F). Screen printing, dispensing, or the like can be used as a method for forming the partition 21. After the partition 21 is formed, firing is performed. A firing temperature needs to be lower than the heat-treatment temperature, at which the intermetallic compound is produced. A heating method and a heating atmosphere for the firing are not particularly limited.

Step 4

Figure 2G:
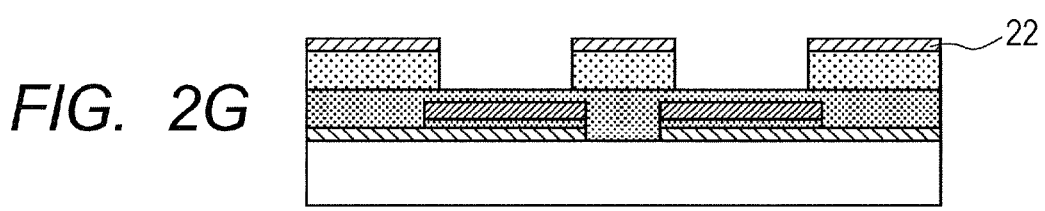

The bonding material 22 is formed on the partition 21 (FIG. 2G). Screen printing, dispensing, or the like can be used as a method for forming the bonding material 22. After the bonding material 22 is formed, heat treatment such as pre-firing is performed, as needed.

Step 5

The through holes 42 as illustrated in FIG. 1A are formed at predetermined locations of the first substrate 11. Each hole 42 is intended for receiving a reagent to pass through the fluid channel 41 or discharging the reagent. A known machining method, such as drilling, sand blasting, or laser machining, can be used for machining the holes 42.

Step 6

Figure 2H:
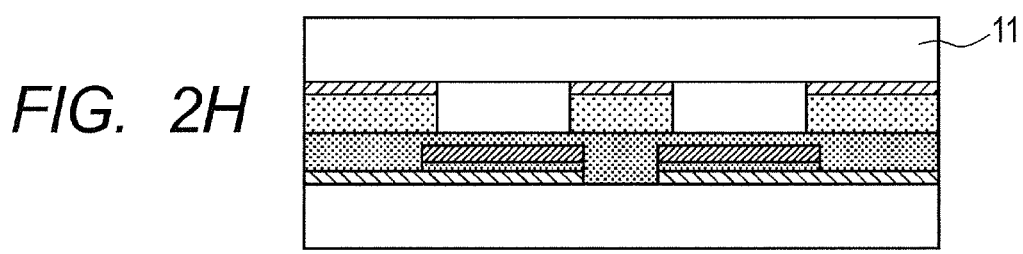

The second substrate 12 fabricated by the steps up to step 4 and the first substrate 11 having the holes formed in step 5 are arranged to as to face each other (FIG. 2H). At this time, the bonding material 22 is pressurized and arranged so as to contact the first substrate 11. The pressurization only needs to be performed such that the bonding material 22 and first substrate 11 contact each other. The first substrate 11 or second substrate 12 may be pressurized with, e.g., a weight or a spring material. During the pressurization, heat treatment is performed Such that the bonding material 22 is softened and melted, and the first substrate 11 and second substrate 12 are seal-bonded with the bonding material 22 between the substrates. The heat treatment is not particularly limited as long as a heating method and a heating atmosphere suitable for the bonding material are suitable for the bonding material.

Note that if an intermetallic compound layer serving as the intermediate layer is formed between the first metal layer and the second metal layer without using an intermediate material, by firing the material for the resistor 33 and the material for the extraction electrode 32, the step of forming the intermediate material 34 can be omitted from step 1. In this case, an intermetallic compound may be produced between the extraction electrode 32 and the resistor 33 by directly forming the resistor 33 on the extraction electrode 32 and performing heat treatment in step 2.

An intermediate material arranged between a resistor and an extraction electrode interdiffuses into the resistor and extraction electrode by heat treatment to produce a specific intermetallic compound at an interface between the intermediate material and the resistor or extraction electrode. An intermetallic compound to be produced depends on the temperature of the heat treatment. Once an intermetallic compound is produced, an element in a layer of the intermetallic compound does not diffuse at a temperature lower than a temperature at which the layer is formed. For this reason, when performing heat treatment at a temperature lower than the production temperature of the intermetallic compound after that, an intermediate layer made of the intermetallic compound acts as a barrier layer which prevents interdiffusion among the intermediate material, resistor, and extraction electrode. In the formed intermediate layer made of the intermetallic compound, no matter how many times heat treatment is performed, no change in electric resistance occurs as long as the heat treatment is performed at a temperature lower than the formation temperature.

In first heat treatment (step 2) for producing an intermetallic compound, since the intermetallic compound is uniformly produced at an interface, the amount of variation in electric resistance is substantially uniform. Accordingly, if variation in electric resistance after the first heat treatment that produces the intermetallic compound is known, the resistance can be easily controlled even in a process which involves a plurality of heat treatment operations.

If the melting point of a produced intermetallic compound is lower than the temperature of heat treatment in a process, the intermetallic compound is melt during the heat treatment. Such intermetallic compound is thus not appropriate as a barrier layer.

Since an intermetallic compound is uniformly produced across an interface by interdiffusion, variation in electric resistance is substantially uniform. Devices formed under the same conditions have the same amount of variation in electric resistance. For this reason, if the electric resistances of some devices are measured in advance before and after heat treatment for producing an intermetallic compound, the amount of variation obtained by the measurement can be applied to devices manufactured under the same conditions.

A device according to the present invention is suitably implemented as, but not limited to, a fluidic device including a fluid channel as described above. The device is also suitably implemented as a device where variation in electric resistance is of concern. The device may be a device including a plurality of open well structures or may be configured as a device which utilizes electrophoresis, dielectrophoresis, or the like.

That is, a device according to another aspect of the present invention is a device including: a first structure which includes a plurality of metal layers stacked on a substrate; and a second structure which is bonded to the substrate and which is obtained by firing glass frit; and the device includes, between a first metal layer and a second metal layer, an intermediate layer of an intermetallic compound containing one or more metallic elements, of which the first metal layer is made, and one or more metallic elements, of which the second metal layer is made, and a melting point of the intermetallic compound is higher than a temperature at which the glass frit is fired. This configuration inhibits metal diffusion at the time of firing the glass frit.

Example 1

Main steps of the present invention will be described below in detail in the context of a specific example. In Example 1, a microfluidic device was manufactured using the manufacturing method according to the embodiment described with reference to FIGS. 2A to 2H.

Step 1 (a step of forming a hole in a first substrate 11 and a step of forming an extraction electrode 32, an intermediate material 34, a resistor 33, and a protective coat 31 on a second substrate 12)

Synthetic quartz substrates which were 4-inch wafers with a thickness of 0.6 mm were prepared as the first substrate 11 and second substrate 12. The surfaces of the first substrate and second substrate were degreased by organic solvent washing, pure water rinsing, and UV/ozone cleaning.

Through holes were formed at positions corresponding to inlets and outlets of microfluid channels in the first substrate 11. As the through holes, holes with a diameter of about 200 µm were formed by laser machining (with a $YVO_4$ laser with a wavelength of 355 nm at a power of 4 W and a frequency of 20 kHz).

A photoresist was applied to the second substrate and was patterned in the shape of the extraction electrodes using a photomask with a pattern of the electrodes. After that, Au (with a purity of 99.9%) was deposited to about 300 nm, and the resist was removed to obtain a desired electrode pattern.

In order to arrange the intermediate material 34 on a part of each extraction electrode where the extraction electrode and the corresponding resistor are to contact, processing is performed in the same manner as the patterning of the electrode portions. More specifically, a photoresist was applied, patterning was performed using a photomask with a pattern of the intermediate materials, and Ti (with a purity of 99.9%) was deposited to about 20 nm by sputtering. The intermediate material was about 300 µm in width and about 200 µm in length.

The resistors 33 were patterned in the same manner as described above, and Pt (with a purity of 99.9%) was deposited to about 100 nm by sputtering. The resistors were about 300 µm in width and about 180 mm in length. As illustrated in FIG. 1A, two resistors were arranged in parallel.

The protective coat 31 was patterned in the same manner as described above so as to entirely cover the resistors. $SiO_2$ was deposited to about 1000 nm by sputtering.

Step 2 (a step of heat-treating the second substrate 12 so that each intermediate material is diffused into the extraction electrode and resistor and an intermetallic compound is produced)

The second substrate 12 was heat-treated in a batch type electric furnace. The heat treatment was performed in the atmosphere at a temperature of about 600° C. for a peak temperature holding time of 10 to 20 min. After the second substrate 12 was held at the peak temperature, the second substrate 12 was cooled over a long period of time. When the second substrate 12 was cooled to substantially the same temperature as room temperature, the second substrate 12 was taken out from the furnace.

Step 3 (a step of forming a partition 21 for microfluid channels on the second substrate 12 and a step of forming a bonding material 22 on the partition 21)

A glass paste material to serve as the partition for microfluid channels was formed on the second substrate having undergone the heat treatment by screen printing, as illustrated in FIG. 2F. In the present example, a photo paste in which an organic matter and a photosensitive resin as binders were dispersed in and mixed with a Bi-based lead-free glass having a softening point of 500° C. as a base material was used as the glass paste material. A solid film without a pattern of the paste was printed on the protective film of the second substrate by screen printing. After that, the solid film was patterned using a photomask with a pattern of a desired microfluid channel partition and was developed with sodium carbonate, and the partition was formed. The microfluid channel partition was formed to be about 200 µm in width. After the partition was formed, heat treatment in the atmosphere was performed in a belt conveyor type continuous furnace at about 500° C. for a peak temperature holding time of 20 to 30 min. The photo paste was fired with the organic matter burnt out.

As illustrated in FIG. 2G, the bonding material was formed by screen printing so as to lie on the partition 21. In the present example, glass frit was used as the bonding material 22. As the glass frit, a paste in which an organic matter as a binder was dispersed in and mixed with a Bi-based lead-free glass frit having a coefficient α of thermal expansion of $75 \times 10^{-7}/°C$ and a softening point of 390° C. as a base material was used. The paste was screen printed using a screen printing plate with a pattern suited to the dimensions of the partition formed at the second substrate. After that, the paste was heated at about 400° C. to burn out the organic matter and was fired.

Step 4 (a step of bonding together the first substrate 11 and second substrate 12)

The second substrate 12 with the bonding material 22 formed was brought into contact with the first substrate 11 with the bonding material 22 between the substrates such that the holes formed in the first substrate 11 were aligned over microfluid channels above the second substrate 12 while being aligned with the first substrate 11, such that the components were temporarily assembled. After that, a block of SUS304 weighing about 40 g was mounted as a weight on the first substrate 11 to apply pressure to the bonding material 22. In this manner, the first substrate 11 and second substrate 12 were brought into contact with the bonding material 22 between the substrates. The first and second substrates 11 and 12 in this state were placed into the belt conveyor type continuous furnace and were heat-treated in the atmosphere at about 460° C. for a peak holding time of 20 to 30 min. The bonding frit was softened and melted to bond together the first substrate 11 and second substrate 12.

In the above-described manner, a microfluidic device was fabricated. The electric resistance of each resistor of the device was measured. A result of the measurement showed that variation in resistance caused by heat treatment after an intermetallic compound was produced was as very small as 0.08% or less, that is, the resistance varied little. Additionally, in the device fabricated according to the present example, all the resistors had the same amount of variation in electric resistance between before and after the heat treatment for intermetallic compound production, and resistance correction could be easily performed.

An exemplary embodiment of a microfluidic device according to the present invention has been specifically described above. The present invention, however, is not limited to the disclosed embodiment. The present invention is not limited to microfluidic devices, and any other device where electric resistance is of concern and which requires high-temperature heat treatment may be used.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-277996, filed Dec. 20, 2011, which is hereby incorporated by reference herein in its entirety.

What is claimed is:

1. A device comprising:
   a first structure, which includes at least first and second metal layers of different compositions on a substrate; and
   a second structure formed by a firing process from a glass-containing material,
   wherein the first structure further comprises an intermediate layer between the first metal layer and the second metal layer,
   wherein the intermediate layer is of an intermetallic compound containing one or more metallic elements, of which the first metal layer is made, and one or more metallic elements, of which the second metal layer is made, and a melting point of the intermetallic compound is higher than a firing temperature required in a subsequent device manufacturing process,
   wherein the first metal layer and the second metal layer are individually patterned such that a single island pattern of the first metal layer overlaps two island patterns of the second metal layer at separate areas on the substrate,
   wherein the intermediate layer is formed at the separate areas between the single island pattern of the first metal layer and the two island patterns of the second metal layer, and
   wherein the first metal layer serves as a heat-generating resister layer and the second metal layer serves as a pair of electrodes each of which is electrically connected to the first metal layer at the separate areas.

2. The device according to claim 1, wherein the melting point of the intermetallic compound is higher than a firing temperature when the second structure is formed.

3. The device according to claim 1, wherein the device is a microfluidic device including a fluid channel.

4. The device according to claim 3, wherein the device includes the fluid channel above the first metal layer.

5. The device according to claim 4, wherein a wall surface of the fluid channel which is placed at an opposite to a side of the first metal layer is made of a material with optical transparency.

6. The device according to claim 5, wherein the fluid channel has side wall surfaces which are obtained by firing one of glass frit and glass paste.

7. A method for manufacturing a device according to claim 1, comprising forming an intermediate layer by forming the first metal layer, the second metal layer, and a layer of an intermediate material which is one of a metallic element and a compound containing a metallic element and which produces an intermetallic compound by interdiffusion between the first metal layer and the second metal layer by firing and, before forming the second structure, firing the first metal layer, the second metal layer, and the layer of the intermediate material at a temperature higher than a firing temperature required in a subsequent process.

8. A method for manufacturing a device according to claim 1, comprising forming the intermediate layer between the first metal layer and the second metal layer by forming the first metal layer and second metal layer and, before forming the second structure, firing the first metal layer and second metal layer at a temperature higher than a firing temperature required in a subsequent process.

9. The device according to claim 1, wherein the intermetallic compound comprises a compound selected from the group consisting of $Ti_3Au$, $AuZr_3$, $V_3Au$, and $AuNb_3$.

10. The device according to claim 1, wherein the first metal layer comprises at least one compound selected from the group consisting of Pt, AuPt, AgPd, and AgRuO,
   wherein the second metal layer comprises a metal or a metal compound containing at least one element selected from the group consisting of Au, Ni, and Pt, and
   wherein the intermediate layer comprises a compound containing at least one element selected from the group consisting of Ti, Zr, B, and Nb.

11. The device according to claim 1, wherein the second metal layer is provided on the substrate such that the second metal layer extends to include and exceed the two separate areas where the first metal layer overlaps the second metal layer.

12. The device according to claim 3, wherein at least one through hole for supplying a liquid to the fluid channel is formed in the substrate.

13. The device according to claim 1, wherein the single pattern of the first metal layer has an elongated shape.

14. The device according to claim 13, wherein the first metal layer is formed into two patterns, which are arranged in parallel, and each of the two patterns has an elongated shape.

15. A device including at least first and second metal layers of different compositions on a substrate,
wherein an intermediate layer is formed between the first metal layer and the second metal layer, the intermediate layer is of an intermetallic compound containing one or more metallic elements, of which the first metal layer is made, and one or more metallic elements, of which the second metal layer is made,
wherein the first metal layer and the second metal layer are individually patterned such that a single island pattern of the first metal layer overlaps two island patterns of the second metal layer at separate areas on the substrate,
wherein the intermediate layer is formed at the separate areas between the single island pattern of the first metal layer and the two island patterns of the second metal layer, and
wherein the first metal layer serves as a heat-generating resister layer and the second metal layer serves as a pair of electrodes each of which is electrically connected to the first metal layer at the separate areas.

16. The device according to claim 15, wherein the device is a microfluidic device including a fluid channel.

17. The device according to claim 16, wherein the device includes the fluid channel above the first metal layer.

18. The device according to claim 17, wherein a wall surface of the fluid channel which is placed at an opposite to a side of the first metal layer is made of a material with optical transparency.

19. The device according to claim 18, wherein the fluid channel has side wall surfaces which are obtained by firing one of glass frit and glass paste.

20. The device according to claim 15, wherein the intermetallic compound comprises a compound selected from the group consisting of $Ti_3Au$, $AuZr_3$, $V_3Au$, and $AuNb_3$.

21. The device according to claim 15, wherein the first metal layer comprises at least one compound selected from the group consisting of Pt, AuPt, AgPd, and AgRuO,
wherein the second metal layer comprises a metal or a metal compound containing at least one element selected from the group consisting of Au, Ni, and Pt, and
wherein the intermediate layer comprises a compound containing at least one element selected from the group consisting of Ti, Zr, B, and Nb.

22. The device according to claim 15, wherein the second metal layer is provided on the substrate such that the second metal layer extends to include and exceed the two separate areas where the first metal layer overlaps the second metal layer.

23. The device according to claim 16, wherein at least one through hole for supplying a liquid to the fluid channel is formed in the substrate.

24. The device according to claim 15, wherein the single pattern of the first metal layer has an elongated shape.

25. The device according to claim 24, wherein the first metal layer is formed into two patterns, which are arranged in parallel, and each of the two patterns has an elongated shape.

* * * * *